United States Patent [19]

George

[11] Patent Number: 5,363,838

[45] Date of Patent: Nov. 15, 1994

[54] FIBEROPTIC INTUBATING SCOPE WITH CAMERA AND LIGHTWEIGHT PORTABLE SCREEN AND METHOD OF USING SAME

[76] Inventor: Gordon P. George, 255 S. Alpine Dr., Alpine, Utah 84004

[21] Appl. No.: 987,673

[22] Filed: Dec. 9, 1992

[51] Int. Cl.⁵ .............................................. A61B 1/04
[52] U.S. Cl. ........................................ 128/6; 126/11; 126/207.14; 346/65
[58] Field of Search .................. 128/10, 11, 207.14, 128/6, 4; 348/65, 74

[56] References Cited

U.S. PATENT DOCUMENTS 4,651,202 3/1987 Arakawa ........................... 128/6 X
4,742,819 5/1988 George ............................ 128/11 X Primary Examiner—Richard J. Apley
Assistant Examiner—Beverly A. Meindl
Attorney, Agent, or Firm—Polster, Lieder Woodruff & Lucchesi

[57] ABSTRACT

A fiberoptic/electronic intubating scope with camera and lightweight portable screen is used for the intubation of the trachea (or other body cavities and lumina) in patients where structures such as laryngeal and tracheal structures are not easily viewed directly using standard devices such as a standard laryngoscope and blade because of anatomic or morphologic irregularities or changes.

25 Claims, 2 Drawing Sheets

FIBEROPTIC INTUBATING SCOPE WITH CAMERA AND LIGHTWEIGHT PORTABLE SCREEN AND METHOD OF USING SAME

BACKGROUND OF THE INVENTION

This invention relates to fiberoptic scopes and, in particular, to an intubation scope having an associated integral lightweight portable screen. It is a modification of my previous invention of an intubation scope with camera and screen, U.S. Pat. No. 4,742,819, dated May 10, 1988, which is incorporated herein by reference.

It is frequently necessary in medical procedures to insert an endotracheal tube into the trachea of a patient for the purpose of performing diagnostic tests or for the introduction of some means of ventilation, oxygenation, and/or airway protection. Even in the best situations, intubation is often difficult and can give rise to complications. In many patients, establishment of the airway may be formidable due to morphologic anomalies such as a large tongue, excessive pharygeal or laryngeal soft tissue, or tracheal displacement, as well as physiologic events such as laryngospasm, regurgitation of gastric materials, blood, or foreign bodies. The morphologic anomalies make it difficult to visualize the posterior pharygeal area and larynx. In emergency situations, attempts to intubate such patients are difficult, time consuming, and often meet with failure. Inability to expeditiously intubate the patient and protect the airway can lead to significant hypoxemia. Cases of death have also been related to complications arising from an intubation process, that were caused by inability to quickly and clearly see the larynx and trachea.

Several attempts have been made to provide an intubating scope which facilitates intubation of a patient. U.S. Pat. No. 3,776,222 to Smiddy, entitled "Fiberoptic Intubator and Method of Intubation of the Trachea through the Nasopharynx," discloses an intubator which facilitates intubation through visual means. That invention involves the introduction of an endotracheal tube through the nasal pharynx, facilitated by an internally disposed fiberoptic scope with a single eyepiece at its proximal end. The Smiddy device was devised for use in situations where the patient could assist in placement of the endotracheal tube by swallowing action (when the patient is in an upright position). In an emergency situation, assistance from the patient, even if he is able to maintain an upright posture, is unlikely. Intubation must be quick and accomplished by mechanical means guided only by the attending physician and/or technician.

U.S. Pat. No. 4,086,919 to Bullard discloses a laryngoscope having a single eyepiece attached to the laryngoscope blade and handle. The eyepiece is illuminated by a fiberoptic system. This device also could be improved. If the attending physician looks through the Bullard scope and has to remove his eyes from the eyepiece to make an external assessment of the airway of the patient, a critical lag in time occurs before the physician can refocus on the internal images seen through the eyepiece. The critical lapse of time caused by the process of focusing and refocusing can affect the timely placement of the endotracheal tube and may even cause the physician to misinterpret certain landmarks, hindering the exact placement of the endotracheal tube. Because the eyepiece is attached to the laryngoscope blade and handle, the physician may not be able to see deep enough into the oral pharynx and larynx to visualize the opening to the trachea. Most importantly, the movement of the physician's body and head, down to, and away from, the eyepiece can lead to erroneous placement of the endotracheal tube in a structure other than the patient's airway because of movement of the blade and handle and thus movement of the visual field of the eyepiece.

Fiberoptic scopes designed specifically for anesthesiologists, such as the scope sold by Olympus under the trade designation LF1, may be used for the intubation of a patient. However, they require techniques that are not usually used by attending physicians unless they are specifically skilled in the use of fiberoptic intubating scopes. The intubation of a patient using a fiberoptic scope with an eyepiece such as an LF1 usually calls for more familiarity than is usually attained by many physicians, and in an emergency situation a physician will tend to return to those techniques and instruments with which he or she is most familiar. Thus, although a scope such as the LF1 may be used for intubation, a physician will rarely, if ever, use a fiberoptic scope such as the LF1 in an emergency situation unless he or she is extremely well skilled in its use prior to the emergency situation. Indeed, the use of a device that is not routinely used by a physician, which calls for techniques other than those with which he or she usually uses to perform the intubating process, can lead to disaster by delaying the intubation process or leading to misposition of the endotracheal tube or failure to intubate the patient.

Further, with the LF1 or similar devices, the physician must often use both hands on the scope, requiring an assistant or other extra persons to help position the patient's head and open the mouth. The user must also look through an eyepiece and then remove his or her eye away from the eyepiece to look directly into the airway to adjust the position of the fiberoptic scope. These devices thus have the same disadvantages discussed above with respect to the Bullard scope. Further, the LF1 scope and other bronchoscopes are not easily portable and require time to set up. The set up and intubation are usually time consuming, and are prone to failure in inexperienced hands.

Fiberoptic scopes have been used in association with screens in other areas of medicine as well. Scopes used for arthroscopy with screens set on a large monitor off to one side of the operating room table are just one example. Another example is the use of fiberoptic scopes for the general surgeon in the performance of laparoscopic cholecystectomy. Again, the screen and monitoring images are removed from the direction of the operation. To use such fiberoptic scopes and devices for the intubation of the trachea, especially in patients who present airways that are extremely difficult and formidable to intubate and protect, is not the optimal answer to the emergency intubation situation. If such a scope is inserted through the endotracheal tube to view the patient's airway structures as the endotracheal tube goes out of sight, the physician has to turn his or her head and/or body in a significant manner to view the associated screen. If structures are seen that are not easily identifiable, the physician then has to turn his or her head and body back to the direct viewing of the airway to see just where the endotracheal tube is placed, and make a proper adjustment of the endotracheal tube in the airway in relation to the anatomic structures that are present. Then, as the endotracheal tube goes out of sight again, the physician again has to turn his or her head and body off to the side to again look at the screen. Since the physician does not view the airway directly and indirectly through the screen at the same time, confusion, lack of orientation of the endotracheal tube and its proper position in the airway can result, potentially leading to failure in an emergency intubating process.

The invention disclosed in my prior patent, U.S. Pat. No. 4,742,819, entitled "Intubating Scope with Camera and Screen", comes closer to achieving those conditions which are vital to assuring quick, accurate and easy placement of the endotracheal tube in a patient. Indeed, this invention allows the physician to use those techniques with which he or she is most familiar when intubating the patient, i.e., the use of a laryngoscope blade and endotracheal tube with a stylet. It allows the physician to almost simultaneously see the patient's airway as viewed directly or indirectly through the scope with camera and screen. It further allows the physician to minimally move his or her eyes during this intubating process so that he or she does not have to turn his or her head or body to visualize indirectly the airway, as would be required with a screen that is set off to the side and not close to the direct line of vision of the task at hand. However, at this time the device of my prior invention is relatively expensive and technologically difficult to produce.

SUMMARY OF THE INVENTION

One object of the invention is to provide an intubating scope which facilitates the intubation of patients, especially patients whose pharynx, larynx and trachea are not easily visualized.

Another object is to provide such an intubating scope which has little or no "learning curve," and may be readily used by physicians.

A third object is to provide such a scope which does not require the physician to turn his or her head away from the scope or direct visual field during intubation.

A fourth object of this invention is to provide such a scope which may be set up quickly and easily.

A fifth object of this invention is to provide such a scope which is self-contained, lightweight, and portable.

A sixth object of this invention is to provide such a scope which allows the physician (or other user) to see almost simultaneously the more superficial structures of the oral pharynx by direct vision and the deeper structures of the larynx and trachea indirectly through the scope.

These and other objects will be apparent to those skilled in the art in light of the following disclosure and accompanying drawings.

The intubating scope herein disclosed is composed of a semi-malleable or flexible tube, a camera housed in said tube, and a lightweight portable screen which may be easily handled and held in one hand by the physician or an assistant or set in any position as desired by the primary physician using the invention. The camera, which is either housed at the proximal end or at the distal end (in the form of a computer chip or other type of integrated circuit) of the semi-malleable or flexible tube, is connected to the lightweight portable screen either by electronic cables or by a fiberoptic system. The semi-malleable or flexible tube is slidably received in a standard hollow endotracheal tube. It preferably but not necessarily extends just beyond the distal end of the endotracheal tube and may serve as a stylet for inserting the endotracheal tube into the trachea. There may also be a ring that tightly fits onto the flexible stylet portion. The ring may be moved along the shaft of the stylet to limit the extent to which the stylet tube may be slidably exposed beyond the endotracheal tube. This is helpful in adapting to different lengths and sizes of endotracheal tubes.

The scope has fiberoptic bundles descending to the distal tip of the flexible tube to provide illumination of the distal structures of the airway and to provide illumination for viewing of the vital structures in the placement process. Light from the illuminated tract travels back through the fiberoptic tube or directly onto the computer chips where the image is focused and projected, through electronics or fiberoptics, onto the lightweight portable screen.

The light source of the fiberoptic bundles and the power source of the camera are preferably provided by a self-contained power source. Alternatively, the apparatus may be powered by means of a peripheral power source plugged into the camera or display unit of the invention.

Varying flexibility and length of the fiberoptic tube allows the device to be used as a bronchoscope in non-emergency situations and for other diagnostic and therapeutic purposes as well as for its primary purpose of being used as a stylet with an associated lightweight portable screen for the intubating of the airway in the emergency situations.

A method of using the scope is also disclosed

BRIEF DESCRIPTION OF THE DRAWINGS

Similar reference characters indicate similar parts throughout the several views of the drawings.

DETAILED DESCRIPTION OF THE PREFERRED EMBODIMENTS

Figure 1:
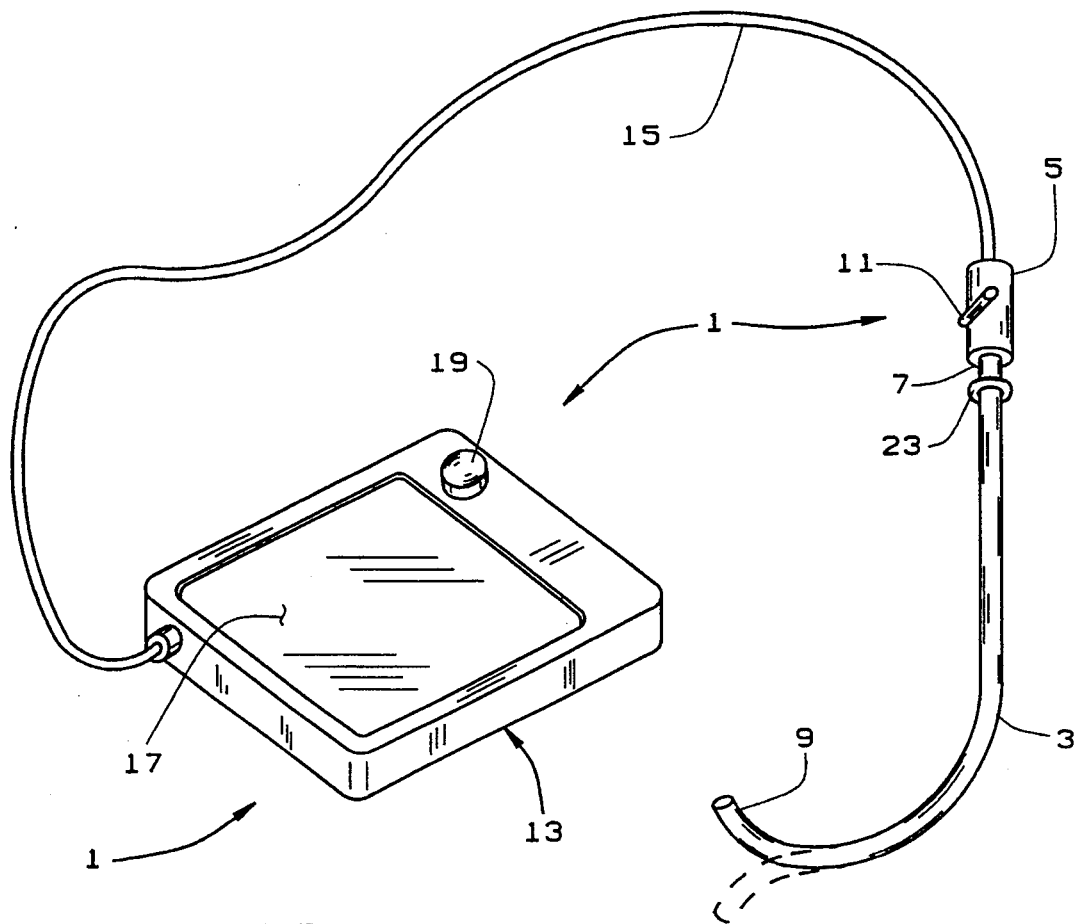
FIG. 1 is a perspective view of an intubating scope of the present invention.
Figure 2:
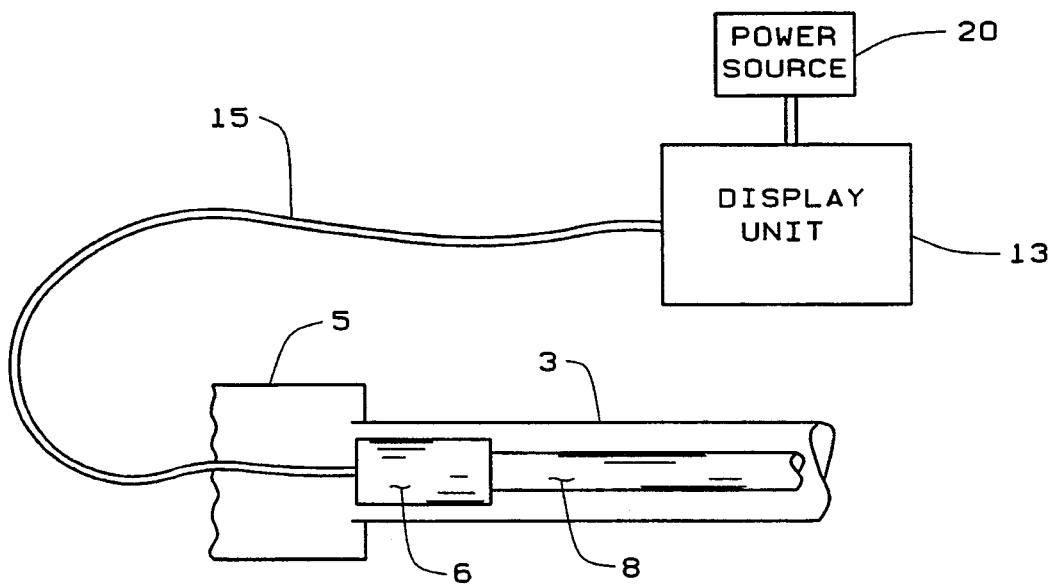
FIG. 2 is a schematic diagram of the intubating scope of FIG. 1.

Referring initially to FIGS. 1 and 2, reference numeral 1 generally refers to an intubation facilitating scope of the present invention. Scope 1 has a semi-malleable tube 3 depending from a handle 5. The semi-malleable tube portion 3 may serve as a stylet. A small optical camera 6 is carried in the tube's proximal end 7. Fiber optic bundles 8 extend the length of tube 3 to allow camera 6 to see internal structures and to provide illumination for the camera to view such internal structures. The camera, alternatively, can be an electronic camera placed at the stylet's distal end 9.

The distal end 9 may be moved to facilitate placement of an endotracheal tube, as will be explained below. A control lever 11 on handle 5 controls the movement of tube distal end 9. The lever 11 is not needed for optimal use of scope 1, but it is preferred.

A very lightweight portable display unit 13 is attached, by way of a wire or fiberoptic cable 15, to camera 6 through handle 5. Unit 13 has a screen 17 which is preferably either a cathode ray tube (CRT) or an LCD screen. It may be black and white or color. An optional control knob 19 is used to adjust contrast, brightness, or any other features. The camera and screen are powered by a power unit 20 which is contained either in display unit 13, in handle 5, or at any other desired location.

Display unit 13, with its self-contained power source in this preferred embodiment, is small and lightweight, as is the entire scope 1. During an intubation procedure, as will be explained below, display unit 13 may be simply placed on the patient's chest or on a boom or a mounting pad next to the physician's line-of-sight of the airway. The display unit may also be easily held in an assistant's or the user's hands, and the entire scope 1 can be quickly carried and placed in the desired position for the physician. This facilitates the physician's viewing and easy focusing of the airway directly and indirectly through the screen.

Figure 3:
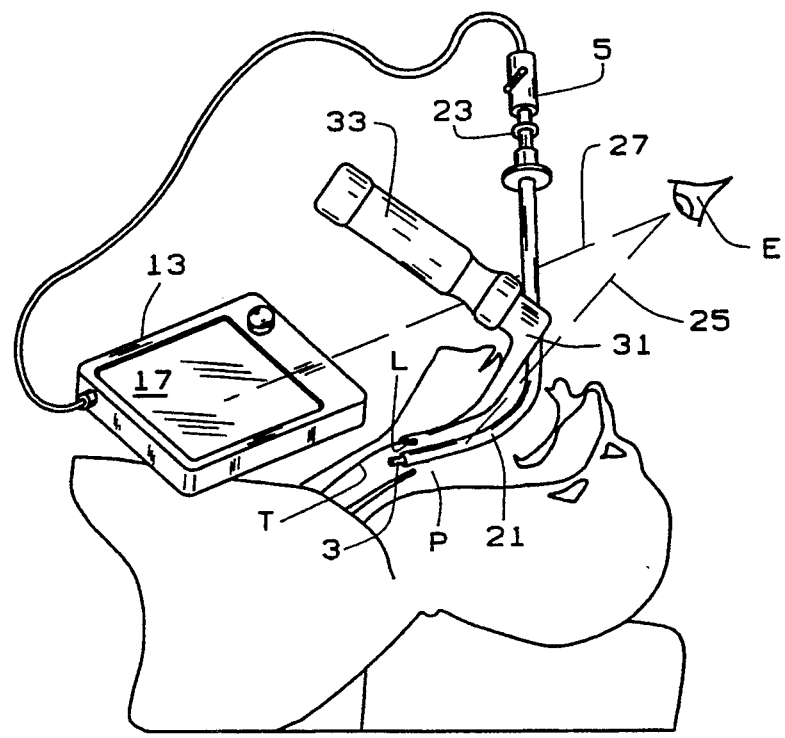
FIG. 3 is an illustration of the scope of FIG. 1 in use, illustrating the physician's lines of sight.

Turning to FIG. 3, the use of scope 1 is described. An endotracheal tube 21 is slidably disposed over the stylet portion 3 until it abuts the handle 5 or a ring 23. The stylet's distal end 9 preferably just barely protrudes from the distal end of endotracheal tube 21. The ring 23 fits snugly around the proximal portion 7 of stylet 3. Ring 23 can move up and down stylet 3 to limit the extent to which the endotracheal tube may be slidably disposed thereon.

The initial placement of the endotracheal tube into the pharynx P and larynx L, and eventually into the trachea T, is facilitated by the use of a standard laryngoscope blade 31 and handle 33 as is usually used by the physicians in the intubating process. After the laryngoscope has been inserted and utilized to open the airway as much as possible, the distal end of endotracheal tube 21, which is slidably disposed over tube 3, is guided into the pharynx and larynx by direct vision as far as is possible, and then guided further into the larynx and trachea by viewing the image illuminated on screen 17. The invention makes it possible for this to be done with little to no movement of the user's eyes, head or body.

Because tube 3 is malleable, it can help the user turn more oblique angles in positioning the endotracheal tube 21 in a difficult airway. The user can also use the lever 11 to control the distal end 9 to aid in the positioning of tube 3 in trachea T, to allow the endotracheal tube 21 to be placed into the trachea T.

Using scope 1, the user is able to look directly into the pharynx and larynx along a direct line-of-sight 25 as shown from a physician's eye E in FIG. 3. As endotracheal tube 21 passes out of the direct line-of-sight 25, the user then glances and moves his or her eyes to the line-of-sight 27 to view the image shown on screen 17 of the lightweight, portable display unit 13, which shows the deeper structures of the larynx and trachea as seen through the camera. After the endotracheal tube is positioned, scope 1 is removed from the endotracheal tube. Thus, the physician can indirectly view the internal structures using camera 6 and display unit 13. Because the display unit is lightweight, it can be placed in any desired place, such as just below the chin of a patient and next to the direct line-of-sight 25. This allows the physician to simultaneously directly view the airway by line-of-sight 25 and indirectly view the deeper structures of the airway on the lightweight portable screen by line-of-sight 27. Thus, the physician can effect an intubation of the airway without having to move his eyes, head or body at all.

Figure 4:
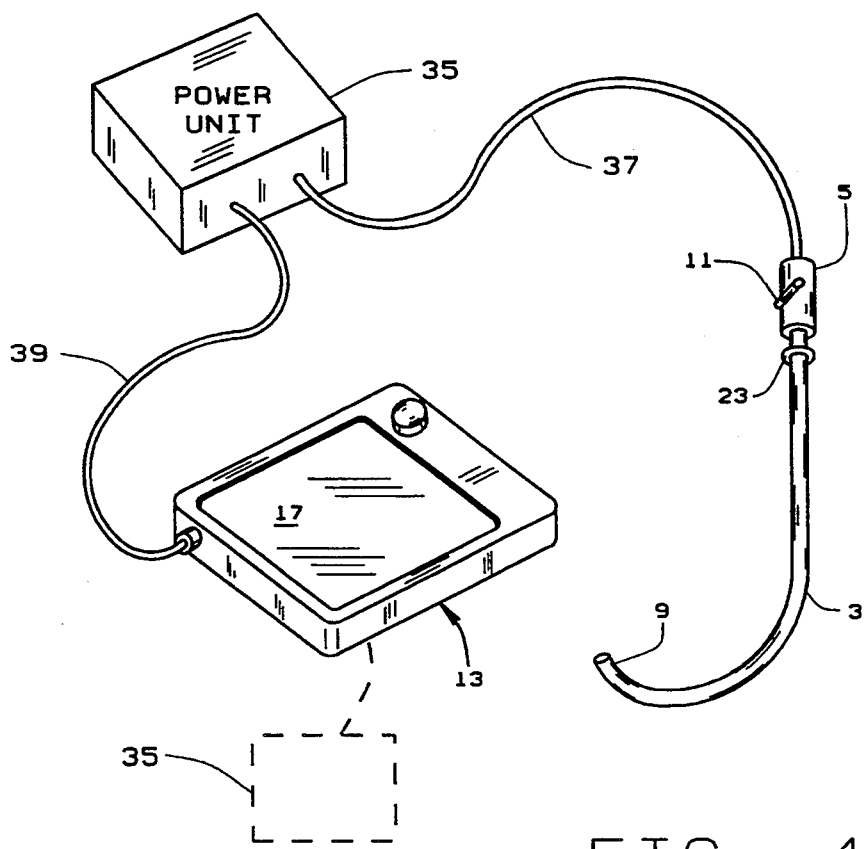
FIG. 4 is an illustration of the use of a second embodiment of the present invention.

FIG. 4 shows a second embodiment of the scope. This is substantially the same as the embodiment of FIGS. 1 and 2. Rather than having an internal power source, however, this embodiment has an external power source 35. In this embodiment, the peripheral power source 35 receives the image from camera 6 in tube 3 over a line 37 and transmits the picture to the lightweight portable display unit 13 over a line 39. Of course, any number of variations of this configuration would also be suitable.

The invention has utility in the intensive care unit, in the operating room, and in the emergency placement of an airway in patients with anatomic, pathophysiologic, or other problems, which would prevent the physician from easily protecting the airway and would prevent ease of placement of an endotracheal tube by standard methods and techniques. Numerous variations in the construction and use of intubating scope 1, within the scope of the appended claims, may occur to those skilled in the art in light of the foregoing disclosure.

Merely by way of example, modifications of scope 1 may allow intubation through either the oral pharynx or nasal pharynx in both emergency and non-emergency situations and intubations where the patient is either conscious or unconscious. It can also be used in the operating room, or other situations such as the confirmation and placement of a double lumen and tracheal tube. A change necessary for other utilizations of the invention would be in stylet 3. Instead of the semi-malleable tube which is used as the stylet in the primary embodiment, the stylet for such other applications would be a freely malleable tube, much like the structure of the tube of a bronchoscope. This modification would allow the scope to be used in many other functions such as esophagoscopy, laparoscopy, or viewing of tissues in the retroperitoneum or to any structures that may not be easily reachable by a laparoscope or other rigid scope.

The invention can be further modified and attached to suction or bovie coagulation instruments for use in problems such as bleeding nasal passages or rebleeding of tonsils. It may be used in the evaluation of distal structures of the oral pharynx or larynx.

The device may also be modified to be used in urological procedures, allowing the physician to not have to bend down to look through an eyepiece. Rather he or she can manipulate the urethra, bladder and ureters by directly viewing the position of the instruments, as well as viewing indirectly what the instruments are doing—looking at them through a screen that is lightweight and easily mountable just above the direct visual field.

Also, as can be appreciated the invention can undergo other modifications allowing it to be used in the other medical and dental specialties. These examples are merely illustrative.

I claim:

1. An intubating scope including a handle, a tube depending from said handle for insertion into a cavity in the human body, camera means operatively connected to record the visual field at the distal end of said tube, and display means operatively connected to said camera means for displaying the output of said camera means at a location adjacent said tubed said display means being separately portable from said handle, whereby the display means is disposed substantially along the line of sight of the user inserting the scope into the human body during use.

2. The scope of claim 1 further including lighting means for illuminating a field of view to be recorded by said camera means.

3. The scope of claim 2 further including and power supply means for supplying power to said display means and said camera means.

4. The scope of claim 3 wherein said power supply means is integral to the scope.

5. The scope of claim 4 wherein said power supply means is a peripheral power source.

6. The scope of claim 5 wherein said power supply means is an external power supply means.

7. The scope of claim 1 further including lever means for manipulating said tube.

8. The scope of claim 1 wherein said display means includes a screen which displays images recorded by said camera.

9. The scope of claim 8 wherein said display means is lightweight.

10. The scope of claim 8 wherein said screen is a cathode ray tube screen or an LCD type screen.

11. The scope of claim 1 wherein said camera means is mounted in a proximal end of said tube, said tube including fiber optic means optically connecting said camera with the distal end of said tube.

12. The scope of claim 11 wherein said fiber optic means include a plurality of optic fibers carried in said tube which extend the length of said tube.

13. The scope of claim 11 wherein said fiber optic means is a fiber optic tube.

14. The scope of claim 11 further including fiber optic means for connecting said display to said tube.

15. The scope of claim 8 wherein said camera means is a computer chip camera, and is located in the distal end of said tube.

16. The scope of claim 15 wherein said display means is electrically connected to said camera.

17. The scope of claim 1 wherein an endotracheal tube is slidably received on said tube, said tube being semi-malleable.

18. The scope of claim 17 wherein said semi-malleable tube is extendible out of the distal end of the endotracheal tube.

19. The scope of claim 1 wherein said scope is lightweight and portable.

20. The scope of claim 1 wherein said display means is quickly and easily movable to a position adjacent the line of sight of the user to the directly viewed visual field.

21. The scope of claim 20 wherein the display means is placed in a position allowing substantially simultaneous visualization of the direct visual field and the visual field indirectly seen through the display means.

22. A method of intubating a patient using an intubating scope, said scope comprising a stylet tube which is slidably received in a medical tube, camera means for viewing internal structures at the distal end of said stylet tube, means for illuminating said internal structures, and display means for displaying the output of said camera; said method comprising the steps of:
   a. opening a cavity in said patient;
   b. placing the display means so that it can be viewed by a physician at the same time said physician views the site of insertion of the scope;
   c. inserting said intubating scope and medical tube in said patient;
   d. viewing said site of insertion and said display screen substantially simultaneously to properly position said medical tube; and
   e. removing said intubating scope after said medical tube is properly positioned.

23. The method as set forth in claim 22 wherein the medical tube in an endotracheal tube, said opening step including opening the patient's air way.

24. The method as set forth in claim 23 wherein the display means is placed adjacent the patient's mouth or nose.

25. The method as set forth in claim 23 wherein the stylet tube is semi-malleable, further including the step of varying the shape of the distal end of the stylet tube to promote insertion of the endotracheal tube.

* * * * *

UNITED STATES PATENT AND TRADEMARK OFFICE
CERTIFICATE OF CORRECTION

PATENT NO. : 5,363,838
DATED : November 15, 1994
INVENTOR(S) : Gordon P. George

It is certified that error appears in the above-indentified patent and that said Letters Patent is hereby corrected as shown below:

Column 6, Line 61, delete "tubed" and insert -- tube --

Signed and Sealed this

Twenty-first Day of February, 1995

Attest:

BRUCE LEHMAN

Attesting Officer     *Commissioner of Patents and Trademarks*

REEXAMINATION CERTIFICATE (4025th)

United States Patent [19]
George

[11] B1 5,363,838
[45] Certificate Issued  Mar. 28, 2000

[54] FIBEROPTIC INTUBATING SCOPE WITH CAMERA AND LIGHTWEIGHT PORTABLE SCREEN AND METHOD OF USING SAME

[76] Inventor: Gordon P. George, 255 S. Alpine Dr., Alpine, Utah 84004

Reexamination Request:
No. 90/004,735, Aug. 29, 1997

Reexamination Certificate for:
Patent No.: 5,363,838
Issued: Nov. 15, 1994
Appl. No.: 07/987,673
Filed: Dec. 9, 1992

[51] Int. Cl.$^7$ ............................................... A61B 1/04
[52] U.S. Cl. ........................... 600/120; 600/160; 600/109; 600/194
[58] Field of Search ..................................... 160/101, 114, 160/117, 118, 120, 160, 109, 194; 128/207.14; 348/65, 74

[56] References Cited

U.S. PATENT DOCUMENTS

| | | |
|---|---|---|
| 4,475,539 | 10/1984 | Konomura . |
| 4,617,915 | 10/1986 | Arakawa . |
| 4,736,733 | 4/1988 | Adair . |
| 4,742,819 | 5/1988 | George . |
| 4,846,153 | 7/1989 | Berci . |
| 4,854,301 | 8/1989 | Nakajima . |

*Primary Examiner*—Beverly M. Flanagan

[57] ABSTRACT

A fiberoptic/electronic intubating scope with camera and lightweight portable screen is used for the intubation of the trachea (or other body cavities and lumina) in patients where structures such as laryngeal and tracheal structures are not easily viewed directly using standard devices such as a standard laryngoscope and blade because of anatomic or morphologic irregularities or changes.

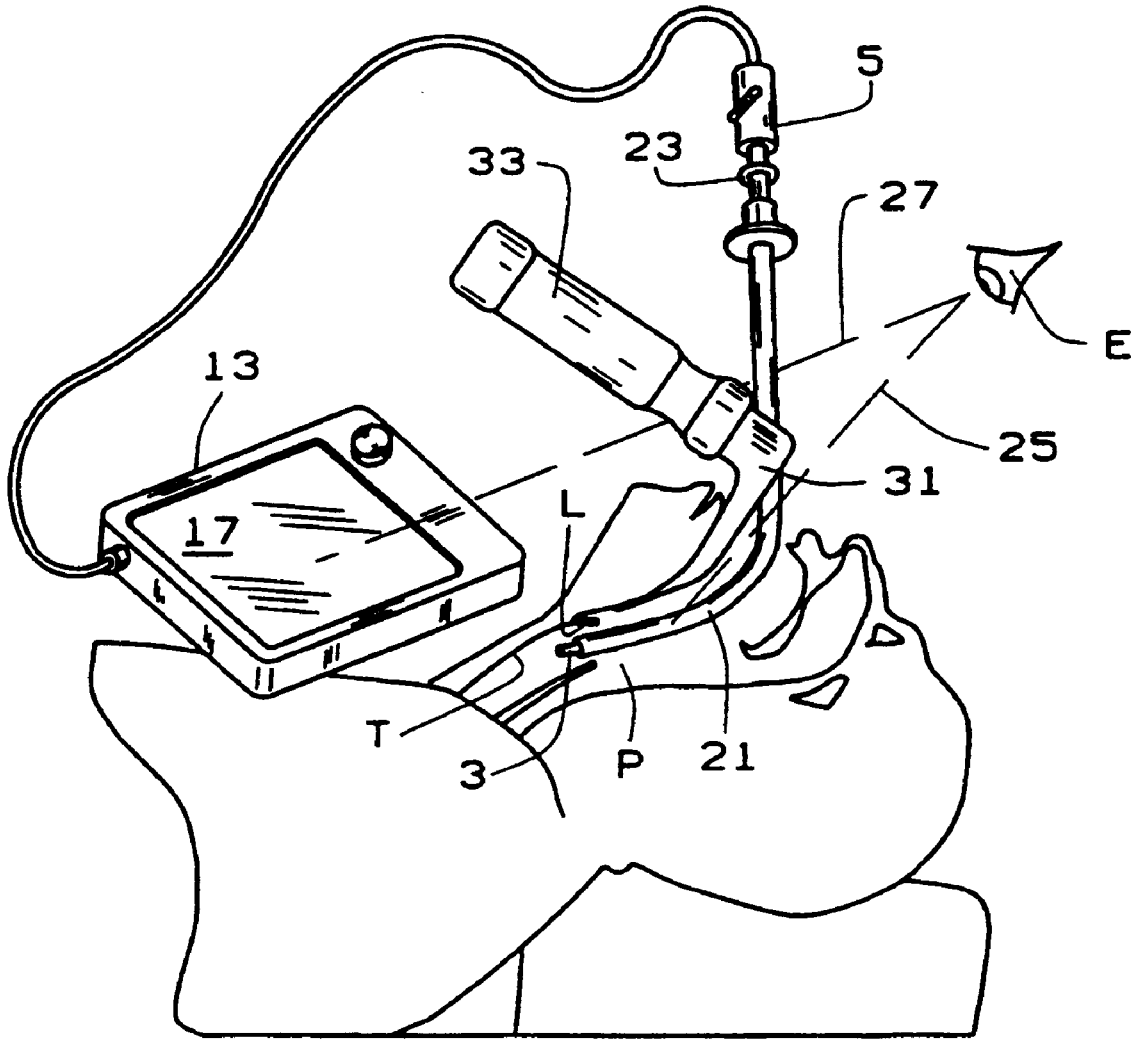

B1 5,363,838

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3–6, 8, 9 and 19–22 are cancelled.

Claims 2, 7, 10 and 11–18, 23–25 are determined to be patentable as amended.

New claims 26–30 are added and determined to be patentable.

2. The scope *system* of claim [1] *29* further including light means for illuminating a field of view to be recorded by said camera means.

7. The scope *system* of claim [1] *29* further including lever means for manipulating said tube.

10. The scope *system* of claim [8] *29* wherein said screen is a cathode ray tube or an LCD type screen.

11. The scope *system* of claim [1] *29* wherein said camera means is mounted in a proximal end of said tube, said tube including fiber optic means optically connecting said camera with the distal end of said tube.

12. The scope *system* of claim 11 wherein said fiber optic [means] *bundle* includes a plurality of optic fibers carried in said tube which extend the length of the tube.

13. The scope *system* of claim 11 wherein said fiber optic [means] *bundle* is a fiber optic tube.

14. The scope *system* of claim 11 further including fiber optic means for connecting said display *means* to said tube.

15. The scope *system* of claim [8] *29* wherein said camera means is a computer chip camera, and is located in the distal end of said tube.

16. The scope *system* of claim 15 wherein said display means is electically connected to said *computer chip* camera.

17. The scope *system* of claim [1] *29* wherein an endotracheal tube is slidably received on said tube, said tube being semi-malleable.

18. The scope *system* of claim 17 wherein said semi-malleable tube is extendible out of the distal end of the endotracheal tube.

23. The method as set forth in claim [22] *30* wherein the medical tube is an endotracheal tube[, said opening step including] *for* opening the patient's air way *and said insertion step comprises inserting the hand-held instrument and medical tube into the patient's mouth and throat to locate said airway.*

24. The method as set forth in claim 23 wherein the [display means] *viewing screen* is placed adjacent the patient's mouth or nose.

25. The method as set forth in claim 23 wherein the [stylet] *tube* is semi-malleable, further including the step of varying the shape of the distal end of the [stylet] *tube* to promote insertion of the endotracheal tube.

26. *A light-weight, easily portable, hand-held fiberoptic scope system comprising:*

*a hand-held instrument comprising, as a single, integrated unit, a handle, a malleable tube depending from said handle and having a distal end for insertion into a cavity in the human body, a fiberoptic bundle running to said distal end, and a camera means operatively connected to record a visual field at said cavity;*

*a light-weight, separately portable display means for placement on or near a patient so as to be near a user's line of sight from the user's eyes to the patient's airway as the hand-held instrument is in use, said display means comprising a viewing screen and a power unit integrated so as to be contained within said display means, and operatively connected to said camera means, said screen and said fiberoptic bundle; and*

*a single cable operatively interconnecting said hand-held instrument and said light-weight, portable display means.*

27. *A light-weight, easily portable, hand-held fiberoptic scope system comprising:*

*a hand-held instrument comprising, as a single, integrated unit, a handle, a malleable tube depending from said handle and having a distal end for insertion into a cavity in the human body, and a fiberoptic bundle running to said distal end;*

*a light-weight, separately portable display means for placement on or near a patient so as to be near a user's line of sight from the user's eyes to the patient's airway as the hand-held instrument is in use, said display means comprising a viewing screen and a power unit integrated so as to be contained within said display means, and operatively connected to said screen, said fiberoptic bundle and a camera means;*

*camera means integrated as a fully contained part of one or the other of said display means, said hand-held instrument or a cable means, and operatively connected to said fiberoptic bundle and to said display means to record a visual field at said cavity; and*

*a cable means operatively interconnecting said hand-held instrument and said light-weight, portable display means.*

28. *A light-weight, easily portable, hand-held fiberoptic scope system comprising:*

*a hand-held instrument comprising, as a single, integrated unit, a handle, a malleable tube depending from said handle and having a distal end for insertion into a cavity in the human body, a fiberoptic bundle running to said distal end, and a camera means operatively connected to said fiberoptic bundle to record a visual field at said cavity;*

*a light-weight, separately portable display means for placement on or near a patient so as to be near a user's line of sight from the user's eyes to the patient's airway as the hand-held instrument is in use, said display means comprising a viewing screen; and*

*a light-weight, separately portable power means for placement on or near a patient, and operatively connected to said camera means, said screen and said fiberoptic bundle.*

29. *A light-weight, easily portable, hand-held fiberoptic, scope system comprising:*

*a hand-held instrument comprising, as a single, integrated unit, a handle, a malleable tube depending from said handle and having a distal end for insertion into a cavity in the human body, and a fiberoptic bundle running to said distal end;*

*a light-weight, separately portable display means for placement on or near a patient so as to be near a user's* line of sight from the user's eyes to the patient's airway as the hand-held instrument is in use, said display means comprising a viewing screen;

a camera means integrated as a fully contained part of one or the other of said display means, said hand-held instrument or cable means, and operatively connected to said fiberoptic bundle and to said display means to record a visual field at said cavity;

a light-weight, separately portable power means for placement on or near a patient, and operatively connected to said camera means, said screen and said fiberoptic bundle; and a cable means operatively interconnecting said hand-held instrument and said light-weight, portable display means.

30. In a light-weight, easily portable, hand-held fiberoptic scope system comprising (a) a hand-held instrument that includes, as a single, integrated unit, a handle, a tube depending from said handle and having a distal end for insertion into a cavity in the human body and having a medical tube slidably engaged thereon, and a fiberoptic bundle running to said distal end, (b) a light-weight, separately portable display means for placement on or near a patient so as to be near a user's line of sight from the user's eyes to the patient's airway as the hand-held instrument is in use, said display means comprising a viewing screen, (c) a camera means integrated as a fully contained part of one or the other display of said means, said hand-held instrument or a cable means, and operatively connected to said fiberoptic bundle and to said display means to record a visual field at said cavity, and (d) a cable means operatively interconnecting said hand-held instrument and said light-weight, portable display means, a method of intubating a patient comprising:

the step of placing the display means on or near the patient so as to be near a user's line of sight from the user's eyes to the patient's airway as the hand-held instrument is in use, so that it can be viewed at the same time the user views the site of insertion of the distal end of the hand-held instrument;

the step of inserting the distal end of the hand-held instrument and medical tube in said patient;

the step of viewing said site of insertion and said viewing screen substantially simultaneously to properly position said medical tube; and the step of removing said hand-held instrument from the cavity and leaving the medical tube in place within the patient after said medical tube is properly positioned.

* * * * *